(12) United States Patent
Sakamoto

(10) Patent No.: US 7,851,160 B2
(45) Date of Patent: Dec. 14, 2010

(54) METHOD FOR DETERMINATION OF AMOUNT OF DOUBLE-STRANDED DNA AND KIT FOR THE DETERMINATION

(75) Inventor: Hatoshi Sakamoto, Niigata (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 250 days.

(21) Appl. No.: 12/085,186

(22) PCT Filed: Nov. 16, 2006

(86) PCT No.: PCT/JP2006/322810

§ 371 (c)(1),
(2), (4) Date: May 16, 2008

(87) PCT Pub. No.: WO2007/066479

PCT Pub. Date: Jun. 14, 2007

(65) Prior Publication Data

US 2009/0136933 A1    May 28, 2009

(30) Foreign Application Priority Data

Nov. 16, 2005    (JP) ............................. 2005-332117

(51) Int. Cl.
*C12Q 1/68*    (2006.01)
*C07H 21/00*    (2006.01)
*G01N 33/48*    (2006.01)
*G01N 33/483*    (2006.01)

(52) U.S. Cl. ..................... 435/6; 536/22.1; 536/23.1; 536/24.3

(58) Field of Classification Search .................. 435/6; 536/22.1
See application file for complete search history.

(56) References Cited

U.S. PATENT DOCUMENTS 6,365,346 B1    4/2002    Patel et al.

6,664,047 B1    12/2003    Haugland et al.

FOREIGN PATENT DOCUMENTS

| JP | 2002-504350 A | | 2/2002 |
| JP | 2002-218998 | * | 8/2002 |
| JP | 2004-257993 | * | 9/2004 |
| JP | 2004-257993 A | | 9/2004 |

OTHER PUBLICATIONS

Malatesta, F. et al: "Potentiometric Characterization of Ethidium Bromide and of Its Reactions With Nucleic Acids" Analytical Biochemistry, Academic Press Inc, New York, vol. 334, No. 1, Nov. 1, 2004, pp. 62-71, XP004583734 ISSN: 0003-2697.

Heli, H. et al: "An Electrochemical Study of Neutral Red-DNA Interaction" Electrochimica Acta, Elsevier Science Publishers, Barking, GB, vol. 51, No. 6, Jul. 15, 2005, pp. 1108-1116, XP005161523 ISSN: 0013-4686.

Maruyama, K. et al: "Detection of Target DNA by Electrochemical Method" Sensors and Actuators B, Elsevier Sequoia S.A., Lausanne, CH, vol. 76, No. 1-3, Jun. 1, 2001, pp. 215-219, XP004241120 ISSN: 0925-4005.

International Search Report dated Aug. 27, 2009.

* cited by examiner

*Primary Examiner*—Ethan Whisenant
(74) *Attorney, Agent, or Firm*—Fitch, Even, Tabin & Flannery

(57) ABSTRACT

A method and kit for electrochemically simply determining with excellent precision the amount of double-stranded DNA does not require an expensive measurement electrode, such as an immobilized enzyme electrode or any high level electrode production technique which can retain uniform surface area accuracy. A method and kit are provided for electrochemically determining the amount of double-stranded DNA in a sample solution based on a residual amount of a substance capable of binding to the double-stranded DNA which is added to the solution in excess amount, in which a buffering substance is added to a sample solution, the buffering substance being capable of allowing an oxidation wave potential of the potential-current curve for the substance capable of binding to the double-stranded-DNA determined in a solution containing the buffering substance to change depending on the concentration of the free substance capable of binding to the double-stranded DNA in the solution.

9 Claims, 2 Drawing Sheets

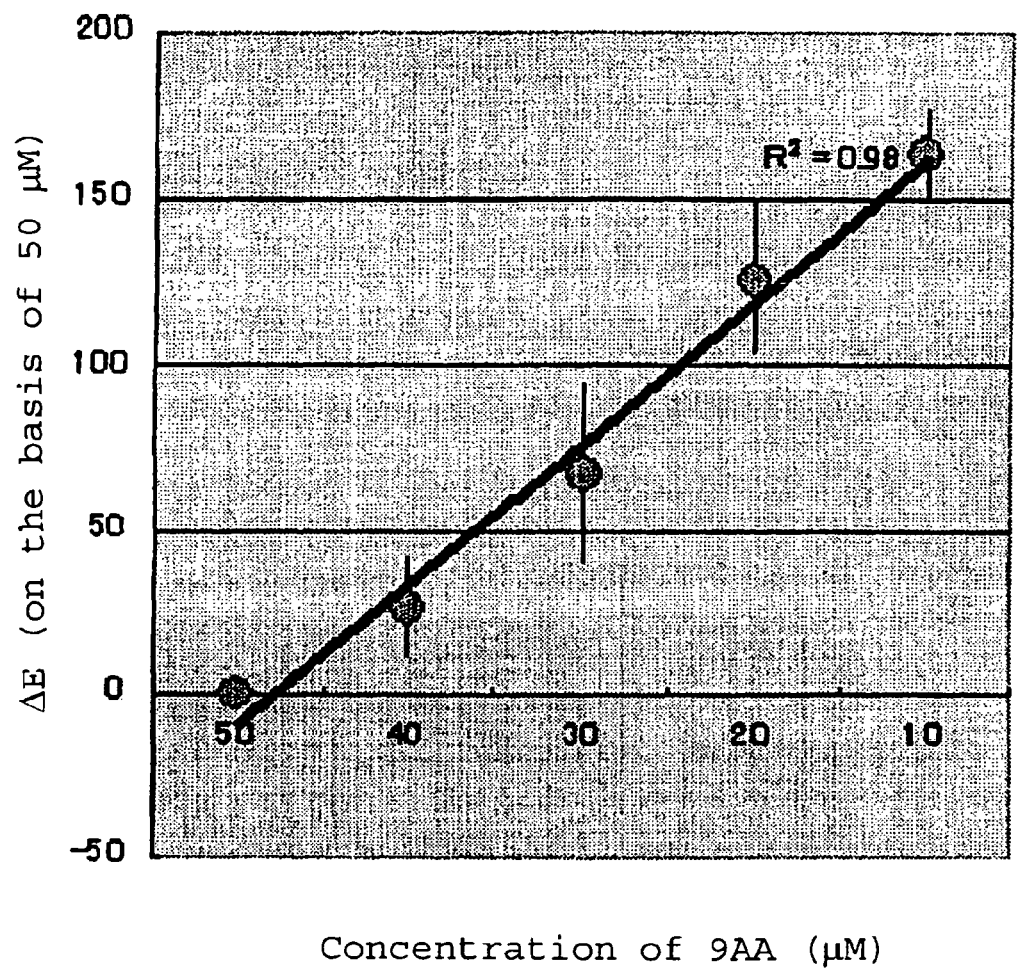
Figure 1: Amount of 9AA and shift amount of oxidation wave potential

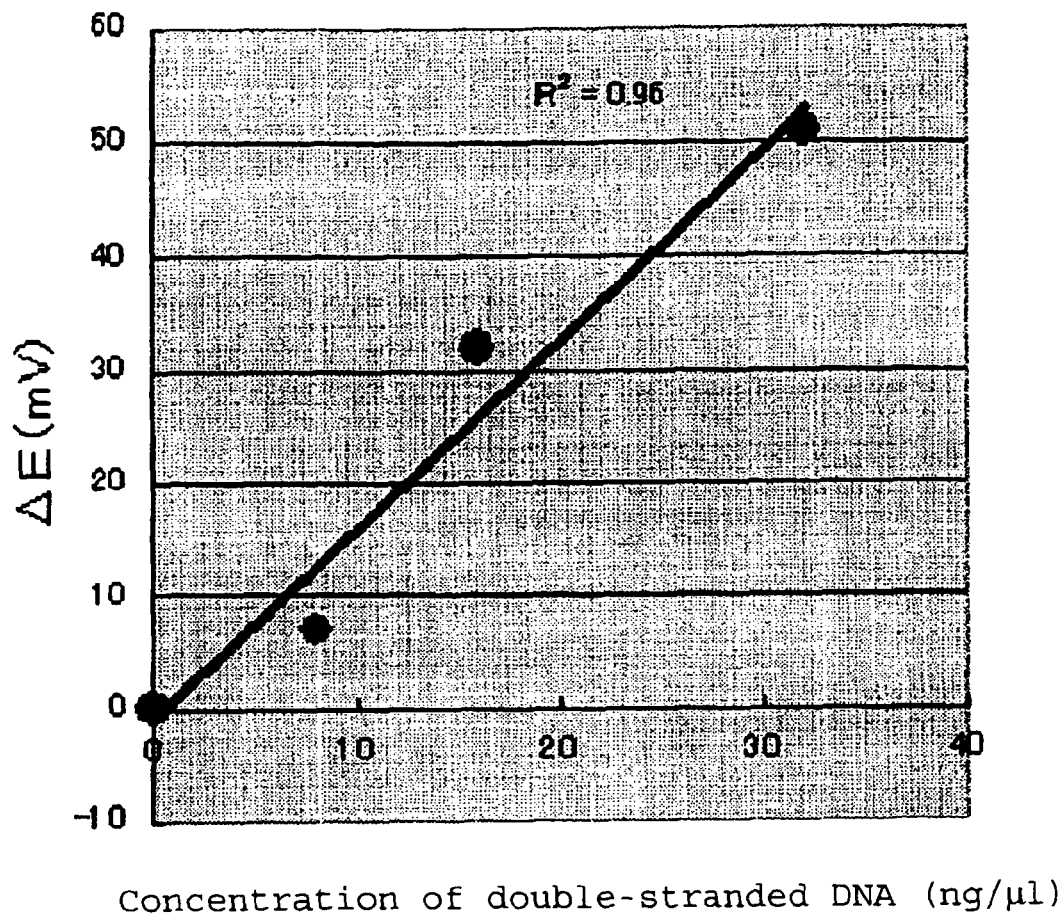
Figure 2: Concentration of double-stranded DNA and shift amount of oxidation wave potential

METHOD FOR DETERMINATION OF AMOUNT OF DOUBLE-STRANDED DNA AND KIT FOR THE DETERMINATION

CROSS-REFERENCE TO RELATED APPLICATION

This is a U.S. National Phase of International Application PCT/JP2006/322810, filed Nov. 16, 2006, and claims the benefit of foreign priority under 35 U.S.C. §119 based on JP 2005-332117, filed Nov. 16, 2005, the entire disclosures of which applications are hereby incorporated herein by reference.

TECHNICAL FIELD

The present invention relates to a method for electrochemically determining the amount of double-stranded DNA contained in a sample in a simple and easy way with precision and a kit for determination of the amount of double-stranded DNA using the above determining method. While it becomes more popular that life activity is understood on a molecular chemistry level and applied to technical developments of medical science, agriculture and the like, efficient methods for determination of the amount of double-stranded DNA and kits for the determination are demanded more and more.

BACKGROUND ART

Hitherto, determination of DNA has placed great importance on detection of a DNA that has a specific nucleotide sequence, and little effort has actually been put into developments of techniques for determining the amount of double-stranded DNA in a sample in a simple and easy way with precision.

Although an absorbance ratio (260/280 nm) in the ultraviolet region is often used for simple determination of DNA, it is greatly influenced by impurities and nucleic acid components other than double-stranded DNA, and thus is low in accuracy for determining double-stranded DNA.

Meanwhile, methods for determining double-stranded DNA only are usually those that measure changes in fluorescence intensity of a substance capable of specifically binding to double-stranded DNA. However, they are problematic in that their background is high and measurable concentration range is narrow, thereby rendering processing of measurement data to be complicated.

In addition to such conventional simple determination methods, methods for determining double-stranded DNA utilizing an electrochemical technique have been developed. For example, there are a method in which a double-stranded DNA is supplemented with a substance capable of specifically binding to the double-stranded DNA so as to detect electrochemical behavior of a complex of the double-stranded DNA and the double-stranded DNA binding substance, and a method in which the amount of the residual double-stranded DNA binding substance which fails to bind to the double-stranded DNA is electrochemically determined (see, for example, Patent Documents 1 and 2).

According to the method disclosed in Patent Document 1, an excess amount of the double-stranded DNA binding substance is added to a sample containing a double-stranded DNA, and then an amount of electrode oxidation current for the free DNA binding substance which fails to bind to the double-stranded DNA is determined so as to obtain the amount of double-stranded DNA. This method requires a high-level technique for manufacturing an electrode since the electrode must always keep the surface area thereof constant with precision so as to detect a weak oxidation current.

According to the method disclosed in Patent Document 2, an immobilized enzyme electrode is used in order to amplify a weak oxidation current on the electrode. However, this method still requires a high-level technique for manufacturing an electrode, and is still problematic in that it requires a sample solution to have a complicated composition since the oxidation-reduction reaction catalyzed by the immobilized enzyme must be conjugated with another reaction so that the reactions proceed reversibly.

Patent Document 1: Japanese Patent Laid-Open No. 2002-218998
Patent Document 2: Japanese Patent Laid-Open No. 2004-257993

DISCLOSURE OF THE INVENTION

Problems to be Solved by the Invention

In light of the above-mentioned circumstances, an object of the present invention is to provide a method for electrochemically determining the amount of double-stranded DNA, which is simple and easy and excellent in accuracy but does not require any expensive measuring electrode such as an immobilized enzyme electrode or any high-level technique for manufacturing an electrode that maintains surface area thereof to be uniform with precision, and to provide a kit for a determination using the above method.

Means for Solving the Problems

As a result of diligent researches for solving the above-mentioned problems of electrochemical determination methods, the present inventor has found a phenomenon that a potential of an oxidation wave (i.e., an oxidation wave potential) of an potential-current curve for a certain double-stranded DNA binding substance, which is determined in a solution containing a specific buffering substance, changes depending on concentration of the double-stranded DNA binding substance, and completed the present invention.

In other words, the present invention relates to a method for electrochemically determining the amount of double-stranded DNA based on a change in a potential of a determined oxidation wave and a kit for determining the amount of double-stranded DNA using the determining method as described in the following (1) to (10), in which the amount of double-stranded DNA is determined by reacting the double-stranded DNA with a substance capable of binding to the double-stranded DNA (i.e., a double-stranded DNA binding substance) and then electrochemically determining the residual amount of the free double-stranded DNA binding substance in the reaction solution, and which is characterized in that a buffering substance is added to the reaction solution, the buffering substance having a property of allowing an oxidation wave potential of a potential-current curve for the double-stranded DNA binding substance determined in a solution containing the buffering substance to change depending upon concentration of the double-stranded DNA binding substance in the solution.

(1) A method for electrochemically determining the amount of double-stranded DNA, which comprises adding, to a solution containing double-stranded DNA, a substance capable of binding to the double-stranded DNA in an excess amount relative to the double-stranded DNA so as to react with each other, and then electrochemically determining the residual amount of the free double-stranded DNA binding substance that fails to bind to the double-stranded DNA so as to determine the amount of the double-stranded DNA contained in the reaction solution, in which the reaction solution contains, as a buffering substance, a substance having a property of allowing an oxidation wave potential of a potential-current curve for the double-stranded DNA binding substance determined in a reaction solution containing the buffering substance to change depending upon concentration of the free double-stranded DNA binding substance in the reaction solution.

(2) The method for electrochemically determining the amount of double-stranded DNA, according to (1), in which the buffering substance is a substance having a property of allowing an oxidation wave potential of a potential-current curve for the double-stranded DNA binding substance determined in a reaction solution containing the buffering substance to shift to a lower potential with decrease of concentration of the free double-stranded DNA binding substance in the reaction solution.

(3) The method for electrochemically determining the amount of double-stranded DNA, according to (1), in which the buffering substance is a substance having a property of allowing an oxidation wave potential of a potential-current curve for the double-stranded DNA binding substance determined in a reaction solution containing the buffering substance to have two or more peaks and allowing the difference in potential between two of the peaks to decrease with decrease of concentration of the free double-stranded DNA binding substance in the reaction solution.

(4) The method for electrochemically determining the amount of double-stranded DNA, according to (1), in which the buffering substance is an alkylsulfonic acid derivative.

(5) The method for electrochemically determining the amount of double-stranded DNA, according to (4), in which the alkylsulfonic acid derivative is one or more selected from the group consisting of 3-morpholinopropanesulfonic acid (MOPS) and N-tris(hydroxymethyl)methyl-3-aminopropanesulfonic acid (TAPS).

(6) The method for electrochemically determining the amount of double-stranded DNA, according to (1), in which the substance capable of binding to double-stranded DNA is an intercalator for double-stranded DNA.

(7) The method for electrochemically determining the amount of double-stranded DNA, according to (6), in which the intercalator is an acridine derivative.

(8) The method for electrochemically determining the amount of double-stranded DNA, according to (7), in which the acridine derivative is 9-aminoacridine.

(9) The method for determining the amount of double-stranded DNA, according to (1), in which the double-stranded DNA is prepared by a reverse transcription reaction from RNA.

(10) A kit for determining the amount of double-stranded DNA using the method for electrochemically determining the amount of double-stranded DNA according to any one of (1) to (9).

Effects of the Invention

According to the present invention, the amount of double-stranded DNA can be determined electrochemically in a simple and easy manner with precision without necessity of any expensive measuring electrode such as an immobilized enzyme electrode or any high-level technique for manufacturing an electrode having a surface area that is maintained uniform with precision.

BEST MODE FOR CARRYING OUT THE INVENTION

The buffering substance used in the present invention may be a substance having a property of allowing an oxidation wave potential of a potential-current curve for a double-stranded DNA binding substance determined in a reaction solution containing the buffering substance to change depending upon concentration of the free double-stranded DNA binding substance in the reaction solution. Especially preferably, the buffering substance is a substance having a property of allowing the oxidation wave potential to shift to a lower potential with decrease of the concentration of the double-stranded DNA binding substance.

The buffering substance having such a property described above is preferably an alkylsulfonic acid derivative, and especially preferably 3-morpholinopropane sulfonic acid (hereinafter, abbreviated as "MOPS") or N-Tris(hydroxymethyl)methyl-3-aminopropane sulfonic acid (hereinafter, abbreviated as "TAPS").

Concentration of the buffering substance such as an alkylsulfonic acid derivative in a solution used in the present invention varies depending on amounts and kinds of DNAs contained in the test sample. The concentration used in a test sample only has to be the same as that used for previously preparing a calibration curve, and determination can be satisfactorily made at a concentration generally used in biochemical studies or examinations, suitably 1 to 200 mM.

The substance capable of binding to double-stranded DNA used in the present invention may bind to the double-stranded DNA in any manner, and is preferably an intercalator which may be inserted into a double-stranded DNA. As such an intercalator, for example, acridine derivatives such as 9-aminoacridine, 3,6-bis (dimethylamino)acridine and 3,6-diamino-2,7-dimethylacridine, are suitably used. Among these, 9-aminoacridine (hereinafter, abbreviated as "9AA") is especially used more suitably.

Amount of the substance capable of binding to double-stranded DNA used in the present invention should be an excess amount relative to double-stranded DNA contained in a solution. For example, when 9AA, an acridine derivative or the like is used to combine with double-stranded DNA, concentration of the residual free double-stranded DNA binding substance which fails to bind to double-stranded DNA is preferably 1 to 500 µM, and more preferably 10 to 200 µM. In the present invention, "free double-stranded DNA binding substance" means a double-stranded DNA binding substance that substantially fails to bind to double-stranded DNA in a solution.

The double-stranded DNA which can be electrochemically determined by the method of the present invention includes, for example, general double-stranded DNA which exists in a solution in a free form, double-stranded DNA formed of a carrier-immobilized single-stranded probe DNA and a sample DNA having a complementary nucleotide sequence, and double-stranded DNA prepared from cDNA which is reverse-transcribed from RNA of an RNA virus such as SRSV, mRNA, rRNA etc. Any double-stranded DNA can be satisfactorily employed.

In the present invention, the change in an oxidation wave potential means, for example, a phenomenon that an oxidation wave at about 1 to 1.5 V potential relative to a silver reference electrode changes in 9AA concentration dependent manner. More particularly, it is a phenomenon that the oxidation wave potential shifts to a lower potential as concentration of 9AA decreases. Such a phenomenon with 9AA is considered to be a summation of the concentration dependent phenomena including stacking phenomenon among 9AA molecules, interaction with a buffering substance, and diffusion on an electrode surface.

In the present invention, the oxidation wave potential is influenced by composition of a sample solution to be determined; however, the amount of double-stranded DNA can be determined satisfactorily by preparing in advance a calibration curve of the amount of double-stranded DNA versus the variation of the oxidation wave potential in a system containing a double-stranded DNA binding substance and a buffering substance to be used for determination. The oxidation wave emerges as a peak of an electric current value of a potential-current curve. The potential corresponding to the summit of the peak may be considered as the oxidation wave potential. However, from a viewpoint of determination accuracy, it is preferred that a potential corresponding to a specific electric current value selected from the range of 50 to 90% of the electric current value of the peak is used as the oxidation wave potential. When a substance that shows two or more peaks in the oxidation wave, such as 9AA, is used, it is preferred that a potential of a peak that changes in the most concentration dependent manner among these peaks is used as the oxidation wave potential. In this case, the amount of double-stranded DNA may be determined by measuring a difference in potential between two peaks and utilizing a variation of the difference.

As a working electrode used for the electrochemical determination of the present invention, a noble metal electrode such as a gold electrode, a gold sputtered electrode and a platinum electrode can be used suitably. As a reference electrode, a silver electrode, a silver-silver chloride electrode and other electrodes may be used as long as electric potential thereof is stable during determination. Such materials as gold, platinum, stainless steel and carbon are used for a counter electrode, and other electrically conductive materials can also be used satisfactorily.

A commonly-used electrochemical technique may be used for the electrochemical determination of the amount of the double-stranded DNA binding substance according to the present invention. No particular restriction is placed thereon as long as an oxidation wave potential for the double-stranded DNA binding substance can be determined based on a relationship between electric potential and electric current.

As the electrochemical determination according to the present invention, cyclic voltammetry (hereinafter, abbreviated as "CV"), linear sweep voltammetry (hereinafter, abbreviated as "LSV") and other electrochemical determinations may be used, whereby the amount of double-stranded DNA can be quantitatively determined based on a change in an oxidation wave potential for a double-stranded DNA binding substance.

Temperature range for the determination according to the present invention is 0° C. to 85° C. at which a double-stranded structure of DNA is maintained, and a binding state of a double-stranded DNA binding substance and a double-stranded DNA is maintained. However, it is generally desirable that the determination is carried out under the temperature range of 4° C. to 45° C. in order to prevent changes in concentration due to moisture evaporation, freezing at a low temperature, and the resulting damage to determination samples.

According to the present invention, the amount of double-stranded DNA contained in a sample can be determined, for example, by the following procedures: diluting a sample containing an unknown amount of double-stranded DNA with a buffer solution containing one or more selected from the group consisting of MOPS and TAPS; adding a constant and excess amount of 9AA; directly inserting therein measuring electrodes consisting of a working electrode, a counter electrode and a reference electrode; and electrochemically measuring free 9AA which fails to bind to double-stranded DNA.

A specific procedure according to the present invention is illustrated as follows: preparing DNA solutions of known double-stranded-DNA concentrations (for example, from 0 to 50 ng/µL) using 10 mM of TAPS and 50 mM of KCl buffer-solution of pH 8.5; adding a constant and excess amount (for example, equivalent to 50 µM) of 9AA; inserting three electrodes, namely, gold electrodes as a working electrode and a counter electrode, and a silver electrode as a reference electrode; and performing CV or LSV. In this example, KCl is added since silver electric potential is more stabilized by the addition of chlorine ion to the determination solution when a silver electrode is used as a reference electrode. However, if a stable electrode is used, KCl does not have to be added.

In the CV, scan is made from the spontaneous potential to $-2$ V relative to the reference electrode potential at a scan rate of 500 mV/s or less, and then immediately up to 2 V relative to the reference electrode at the same rate. If the spontaneous potential of an electrode is stable, LSV determination in which scan is made from the spontaneous potential to 2 V relative to the reference electrode at a scan rate of 500 mV/s or less may be performed.

In this instance, a peak potential of an oxidation wave is determined. The oxidation wave is detected at 1 V to 1.6 V relative to the silver reference electrode potential on a current curve of water decomposition. A peak top may be measured as the peak potential of the oxidation wave; however, since it may be influenced by a concentration of buffer solution constituents, impurities, etc., a potential should be measured at a certain percentage of the peak current value, for example, a predetermined electric current value of 50% to 90% of the peak current value. Alternatively, a method in which the potential is measured based on a differential value of an obtained potential-current curve on certain conditions may be used.

On the basis of the potential obtained in this way, a calibration curve as a standard is prepared using samples that each exhibit a potential variation at a double-stranded DNA concentration relative to a reference potential which is determined, for example, at a DNA concentration of 0 ng/µL.

Using this calibration curve, a concentration of double-stranded DNA is determined from a potential variation relative to the reference potential, in which the potential variation is obtained for a sample to be examined in the same manner as above.

When the sample to be examined is high in double-stranded DNA concentration, the sample may be diluted with a determination solution described above (a buffer solution and a 9AA solution) prior to determination. When an alkylsulfonic acid derivative such as TAPS and MOPS is sufficiently contained in the sample solution, no alkylsulfonic acid derivative has to be added. When an alkylsulfonic acid derivative is not contained in the sample solution, a certain quantity (for example, equivalent to 10 mM) of TAPS, MOPS or the like is properly added, whereby determination can be made well.

The kit for determining double-stranded DNA according to the present invention may comprise, for example, measurement reagents including a substance capable of binding to double-stranded DNA and a buffering substance, and electrochemical measuring means such as electrodes. As the buffering substance, the following substance is used: a substance having a property of allowing an oxidation wave potential of a potential-current curve for the double-stranded DNA binding substance determined in a solution containing the buffering substance to change depending upon concentration of the free double-stranded DNA binding substance in the solution.

More concretely, a kit for determining double-stranded DNA in a simple and easy manner with precision utilizing the present method can be formed and provided by using measurement reagents composed of an alkylsulfonic acid derivative and an acridine derivative, and measuring electrodes composed of three electrodes, namely a noble metal electrode such as of gold and platinum as a working electrode, a reference electrode, and a counter electrode.

A concrete kit may be composed of, for example, 100 μM of 9AA aqueous solution and 20 mM of TAPS buffer solution as measurement reagents, and a measuring electrode which has a counter electrode and a working electrode gold-sputtered on a resin sheet as well as an electrode which has a reference electrode formed of printed silver paste. The kit may be accompanied by a double-stranded DNA as a standard. Moreover, the kit may include a test tube, a vial container, a microplate, etc. for mixing measurement reagents with a sample solution, and micropipette etc. for liquid sampling.

Using the kit according to the present invention, the amount of double-stranded DNA contained in a sample can be determined in a simple and easy manner with precision by the following procedures: mixing measurement reagents with a sample solution; dropping a portion of the mixed solution on measuring electrodes; conducting a scan using a commercially available electric potential applying devices such as a potentiostat device; and determining a difference from the blank value in the oxidation wave potential of a potential-current curve.

EXAMPLES

Hereinafter, the present invention will be described in detail by way of Examples and Comparative Examples. However, the present invention is not limited to these Examples.

Example 1

TAPS buffer solutions (10 mM TAPS, 50 mM KCl, pH 8.5) containing 0 to 40 ng/μL of double-stranded DNA were prepared. As the double-stranded DNA, double-stranded DNA of 80 to 4900 base pairs for electrophoresis markers was used. 2.5 μL of a 9AA aqueous solution (1 mM) was added to 47.5 μL of the double-stranded-DNA solution, and then electrochemical determinations were carried out. The electrochemical determinations were in accordance with an LSV determination which was performed from the spontaneous potential to 2 V using a silver wire as a reference electrode and gold sputtered electrodes (1 mm$^2$ of electrode surface area) as a working electrode and a counter electrode. The oxidation wave potential was determined at an 80% electric current value of the oxidation wave of about 1.2 V relative to the silver reference electrode. Taking the oxidation wave potential ($E_0$) at a double-stranded-DNA concentration of 0 ng/μL as a baseline, differences (ΔE) between the potential ($E_0$) and the oxidation wave potentials ($E_n$) at each double-stranded-DNA concentration were determined, and a calibration curve ($R^2$=0.96) of ΔE versus double-stranded-DNA concentration was prepared. Then, 5 μL of a TAPS buffer solution (100 mM TAPS, 500 mM KCl, pH 8.5) and 2.5 μL of a 9AA aqueous solution (1 mM) were added to 42.5 μL of a sample with an unknown double-stranded-DNA concentration, and an electrochemical determination was carried out in the same manner as above. A potential difference ΔE from $E_0$ was determined. Based on the calibration curve, the amount of double-stranded DNA of this sample was found to be 20±2 ng/μL (n=4).

Example 2

A calibration curve was prepared using a MOPS buffer solution (10 mM MOPS, 50 mM KCl, pH 8.5) in place of the TAPS buffer solution in Example 1. Similarly to the above, 5 μL of a MOPS buffer solution (100 mM MOPS, 500 mM KCl, pH 8.5) and 2.5 μL of a 9AA aqueous solution (1 mM) were added to 42.5 μL of the same sample with unknown concentration as used in Example 1. A potential difference ΔE from $E_0$ was determined by carrying out the same electrochemical determination as above. Based on the calibration curve, the amount of double-stranded DNA of this sample was found to be 20 ng/μL.

Example 3

LSV determinations were performed from the spontaneous potential to 2 V (relative to the silver reference electrode) using 10 mM TAPS buffer solutions (pH 8.5) containing 10 to 50 μM 9AA. Gold sputtered electrodes (1 mm$^2$) were used as a counter electrode and a working electrode.

Taking the oxidation wave potential of a solution containing 50 μM 9AA as a baseline, an amount by which the oxidation wave potential was shifted to the lower potential at each 9AA concentration was determined. A correlation ($R^2$=0.98) was found between the 9AA concentration and the shift amount of the potential (FIG. 1).

Then, TAPS buffer solutions (pH 8.5) containing 0 to 30 ng/μL λDNA were prepared, and 9AA equivalent to 50 μM was added to each solution. LSV determinations were carried out in the same manner as above, and shift amounts were determined based on the oxidation wave potential for the λDNA-free solution. A correlation was found between the amount of λDNA and the shift amounts of the potential ($R^2$=0.96) (FIG. 2).

Example 4

LSV determinations were performed from the spontaneous potential to 2 V (relative to the silver reference electrode) using 10 mM TAPS buffer solutions (pH 8.5) containing 10 to 50 μM 9AA. Gold sputtered electrodes (1 mm$^2$) were used as a counter electrode and a working electrode. Oxidation wave potentials were determined at 90% electric current values of the oxidation wave of about 1.2 V and about 0.65 V relative to the silver reference electrode. Subsequently, a difference between the two oxidation wave potentials was determined.

Taking the difference between the two oxidation wave potentials for a solution containing 50 μM 9AA as a baseline, an amount by which the difference between the two oxidation wave potentials was reduced at each 9AA concentration was determined. A correlation ($R^2$=0.98) was found between the 9AA concentration and the variation of the difference between the two potentials.

Then, TAPS buffer solutions (pH 8.5) containing 0 to 30 ng/μL λDNA were prepared, and 9AA equivalent to 50 μM was added to each solution. LSV determinations were carried out in the same manner as above, and a reduction amount of each difference between the two potentials were determined based on the difference between the two oxidation wave potentials for the λDNA-free solution. A correlation was found between the amount of λDNA and the reduction amounts of the differences between the oxidation wave potentials ($R^2=0.95$).

Example 5

(a) One μL of pSPTetRNA (product of Life Sciences, Inc.) solution was added to 19 μL of a reverse transcription reaction solution containing 5 mM $MgCl_2$, 10 mM TAPS-NaOH (pH 8.5), 50 mM KCl, 1 mM dNTP, 2.5 μM random 9mer primer and 0.25 U/μL AMV Reverse Transcriptase (product of Takara Bio, Inc.). In order to prevent thermal denaturation of the template RNA and reverse-transcribed DNA oligomers, which occurs in early stages of a reverse transcription reaction, reverse transcription reaction was first carried out for 10 minutes at 30° C. and then carried out for 15 minutes at 45° C. Thereafter, the reaction solution was heated for 10 minutes at 99° C. and then ice-cooled in order to deactivate activity of the reverse transcriptase that had become unnecessary.

(b) Then, 20 μL of the reaction solution prepared in the above (a) was added to 80 μL of a PCR reaction solution containing 3.2 mM $MgCl_2$, 12.5 mM TAPS-NaOH (pH 8.5), 62.5 mM KCl, 0.03 U/μL of DNA polymerase, 0.25 μM sense primer (5'-CTGCTCGCTTCGCTACTTGGA-3') and 0.25 μM antisense primer (5'-CGGCACCTGTCCTACGAGTTG-3'). Then, 50 μL of the solution was heated at 95° C. for 2 minutes. Without cooling it down, polymerase chain reaction (PCR) was performed, in which denaturation, annealing and chain-extension were performed at 95° C., 60° C. and 72° C., respectively. The cycle was repeated 30 times.

(c) Using 50 μL of the remaining reaction solution which was not used for the PCR reaction of the above (b), LSV determination was performed with the measuring electrodes from the spontaneous potential to 2 V, and oxidation wave potential $E_0$ was obtained. Then, the reaction sample solution which had been subjected to the PCR was determined in the same manner, and oxidation wave potential $E_1$ was obtained. The measuring electrodes were composed of a working electrode and a counter electrode which were electrodes having gold sputtered on a polyethylene terephthalate resin film, and a reference electrode which was an electrode printed with silver paste. Potential difference ΔE between $E_0$ and $E_1$ was 35 mV. A λDNA calibration curve was previously prepared using solutions of λDNA in a liquid having the same composition as the above reaction solution. From the λDNA calibration curve, it was confirmed that the amount of double-stranded DNA generated from pSPTetRNA was 25 ng/μL as λDNA equivalent.

INDUSTRIAL APPLICABILITY

The method for determining the amount of double-stranded DNA and the kit for determination according to the present invention enable quantitative determination based on a change in a potential of a potential current curve. Thus, the present invention makes a highly precise determination possible, which is not dependent upon the surface area of electrodes unlike conventional electrochemical determination methods which were based on a change of a current amount. The present invention does not require any expensive measuring electrode such as an immobilized enzyme electrode or a high-level electrode manufacturing technique for maintaining uniform surface area accuracy. The present invention can be carried out in a simple and easy manner with precision for determination of the amount of synthesized or extracted double-stranded DNA, or double-stranded DNA amplified by PCR etc.

BRIEF DESCRIPTION OF THE DRAWINGS

FIG. 1 is a graph showing the relationship between the 9AA concentration and the shift amount of oxidation wave potential in a reaction mixture; and FIG. 2 is a graph showing the relationship between the concentration of double-stranded DNA and the shift amount of oxidation wave potential.

The invention claimed is:

1. A method for electrochemically determining the amount of double-stranded DNA, which comprises adding, to a solution containing double-stranded DNA, a substance capable of binding to the double-stranded DNA in an excess amount relative to the double-stranded DNA so as to react with each other, and then electrochemically determining the residual amount of the free double-stranded DNA binding substance that fails to bind to the double-stranded DNA so as to determine the amount of the double-stranded DNA contained in the reaction solution, in which the reaction solution contains, as a buffering substance, a substance having a property of allowing an oxidation wave potential of a potential-current curve for the double-stranded DNA binding substance determined in a reaction solution containing the buffering substance to change depending upon concentration of the free double-stranded DNA binding substance in the reaction solution.

2. The method for electrochemically determining the amount of double-stranded DNA, according to claim 1, in which the buffering substance is a substance having a property of allowing an oxidation wave potential of a potential-current curve for the double-stranded DNA binding substance determined in a reaction solution containing the buffering substance to shift to a lower potential with decrease of concentration of the free double-stranded DNA binding substance in the reaction solution.

3. The method for electrochemically determining the amount of double-stranded DNA, according to claim 1, in which the buffering substance is a substance having a property of allowing an oxidation wave potential of a potential-current curve for the double-stranded DNA binding substance determined in a reaction solution containing the buffering substance to have two or more peaks and allowing the difference in potential between two of the peaks to decrease with decrease of concentration of the free double-stranded DNA binding substance in the reaction solution.

4. The method for electrochemically determining the amount of double-stranded DNA, according to claim 1, in which the buffering substance is an alkylsulfonic acid derivative.

5. The method for electrochemically determining the amount of double-stranded DNA, according to claim 4, in which the alkylsulfonic acid derivative is one or more selected from the group consisting of 3morpholinopropanesulfonic acid (MOPS) and N-tris(hydroxyl-methyl)methyl-3-aminopropanesulfonic acid (TAPS).

6. The method for electrochemically determining the amount of-double-stranded DNA, according to claim 1, in which the substance capable of binding to double-stranded DNA is an intercalator for double-stranded DNA.

7. The method for electrochemically determining the amount of double-stranded DNA, according to claim 6, in which the intercalator is an acridine derivative.

8. The method for electrochemically determining the amount of double-stranded DNA, according to claim 7, in which the acridine derivative is 9-aminoacridine.

9. The method for determining the amount of double-stranded DNA, according to claim 1, in which the double-stranded DNA is prepared by a reverse transcription reaction from RNA.

* * * * *

UNITED STATES PATENT AND TRADEMARK OFFICE
CERTIFICATE OF CORRECTION

| | | |
|---|---|---|
| PATENT NO. | : 7,851,160 B2 | Page 1 of 1 |
| APPLICATION NO. | : 12/085186 | |
| DATED | : December 14, 2010 | |
| INVENTOR(S) | : Hitoshi Sakamoto | |

It is certified that error appears in the above-identified patent and that said Letters Patent is hereby corrected as shown below:

Title Page, Item (75) Inventor: please change inventor name from "Hatoshi Sakamoto" to --Hitoshi Sakamoto--.

Signed and Sealed this
Eighth Day of March, 2011

David J. Kappos
*Director of the United States Patent and Trademark Office*